US00PP30288P2

(12) United States Plant Patent
Kobayashi

(10) Patent No.: US PP30,288 P2
(45) Date of Patent: Mar. 12, 2019

(54) **NEW GUINEA *IMPATIENS* PLANT NAMED 'DUESSPRSPK'**

(50) Latin Name: *Impatiens hawkeri*
Varietal Denomination: Duessprspk

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/732,930

(22) Filed: Jan. 12, 2018

(51) Int. Cl.
*A01H 5/02* (2018.01)

(52) U.S. Cl.
USPC ..... Plt./318.7
CPC ..... *A01H 5/02* (2013.01)

(58) Field of Classification Search
USPC ..... Plt./318.7
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Impatiens* plant named 'Duessprspk' characterized by its moderately compact, upright, outwardly spreading and mounding plant habit; vigorous growth habit; freely branching habit; dark green-colored leaves; freely and early flowering habit; dark rose pink-colored flowers; and good garden performance.

1 Drawing Sheet

Botanical designation: *Impatiens hawkeri.*
Cultivar denomination: 'DUESSPRSPK'.

CROSS-REFERENCED TO CLOSELY-RELATED APPLICATIONS

Title: New Guinea *Impatiens* Plant Named 'DUESSP-PINK'
Applicant: Ruth Kobayashi
Filed: Concurrently with this application Ser. No. 15/732,931

BACKGROUND OF THE INVENTION

The present invention relates to a new and distinct cultivar of New Guinea *Impatiens* plant, botanically known as *Impatiens hawkeri* and hereinafter referred to by the name 'Duessprspk'.

The new *Impatiens* plant is a product of a planned breeding program conducted by the Inventor in Encinitas, Calif. The objective of the breeding program is to create new early and freely flowering New Guinea *Impatiens* plants with attractive flowers and good garden performance.

The new *Impatiens* plant is a naturally-occurring whole plant mutation of a proprietary selection of *Impatiens hawkeri* identified as code number NN-0032-X0012-X0001, not patented. The new *Impatiens* plant was discovered and selected by the Inventor as a single flowering plant from within a population of plants of the mutation parent in a controlled greenhouse environment in Encinitas, Calif. on Dec. 6, 2016.

Asexual reproduction of the new *Impatiens* plant by terminal vegetative cuttings in a controlled greenhouse environment in Encinitas, Calif. since Dec. 13, 2016 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Duessprspk'. These characteristics in combination distinguish 'Duessprspk' as a new and distinct *Impatiens* plant:

1. Moderately compact, upright, outwardly spreading and mounding plant habit.
2. Vigorous growth habit.
3. Freely branching habit.
4. Dark green-colored leaves.
5. Freely and early flowering habit.
6. Dark rose pink-colored flowers.
7. Good garden performance.

Plants of the new *Impatiens* can be compared to plants of the mutation parent selection. Plants of the new *Impatiens* differ primarily from plants of the mutation parent selection in flower color as plants of the mutation parent selection have scarlet orange-colored flowers.

Plants of the new *Impatiens* can be compared to plants of *Impatiens hawkeri* 'Duessppink', disclosed in U.S. Plant patent application Ser. No. 15/732,931 filed concurrently. Plants of the new *Impatiens* differ primarily from plants of 'Duessppink' in flower color as plants of 'Duessppink' have lighter rose pink-colored flowers.

Plants of the new *Impatiens* can be compared to plants of *Impatiens hybrida* 'SAKIMP033', disclosed in U.S. Plant Pat. No. 26,669. In side-by-side comparisons, plants of the new *Impatiens* differ primarily from plants of 'SAKIMP033' in the following characteristics:

1. Plants of the new *Impatiens* are not as compact as plants of 'SAKIMP033'.
2. Leaves of plants of the new *Impatiens* are darker green in color than leaves of plants of 'SAKIMP033'.

3. Plants of the new *Impatiens* and 'SAKIMP033' differ in flower color as plants of 'SAKIMP033' have dark red purple-colored flowers.

Plants of the new *Impatiens* can be compared to plants of *Impatiens hybrida* ' SAKIMP031', disclosed in U.S. Plant Pat. No. 26,806. In side-by-side comparisons, plants of the new *Impatiens* differ primarily from plants of 'SAKIMP031' in the following characteristics:

1. Plants of the new *Impatiens* are more upright than and not as spreading as plants of 'SAKIMP031'.
2. Plants of the new *Impatiens* and 'SAKIMP031' differ in flower color as plants of 'SAKIMP031' have pink-colored flowers.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph at the bottom of the sheet comprises a side perspective view of a typical flowering plant of 'Duessprspk' grown in a container.

The photograph at the top of the sheet is a close-up view of a typical flowering plant of 'Duessprspk'.

DETAILED BOTANICAL DESCRIPTION

The aforementioned photographs and following observations, measurements and values describe plants grown during the summer and early autumn in 16.5-cm containers in a polyethylene-covered greenhouse in Encinitas, Calif. and under cultural practices typical of commercial New Guinea *Impatiens* production. During the production of the plants, day temperatures averaged 26° C., night temperatures averaged 18° C. and light levels ranged from 4,500 to 5,500 lux. Plants were 16 weeks old when the photographs and description were taken. In the following description, color references are made to The Royal Horticultural Society Colour Chart, 2007 Edition, except where general terms of ordinary dictionary significance are used.

Botanical classification: *Impatiens hawkeri* 'Duessprspk'.

Parentage: Naturally-occurring whole plant mutation of a proprietary selection of *Impatiens hawkeri* identified as code number NN-0032-X0012-X0001, not patented.

Propagation:

*Type*.—By terminal vegetative cuttings.

*Time to initiate roots, summer and winter*.—About five to seven days at temperatures about 20° C.

*Time to produce a rooted young plant, summer and winter*.—About three weeks at temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Moderately compact, upright to outwardly spreading and mounding plant habit; freely branching habit with about four to five primary lateral branches each with about four to six secondary lateral branches developing per plant; vigorous growth habit and rapid growth rate.

*Height, soil level to top of foliar plane*.—About 24 cm.

*Height, soil level to top of floral plane*.—About 26 cm.

*Plant diameter or spread*.—About 55 cm.

Lateral branch description:

*Length*.—About 24 cm.

*Diameter, primary lateral branches*.—About 1.8 cm.

*Diameter, secondary lateral branches*.—About 1.3 cm.

*Internode length*.—About 5.3 cm.

*Strength*.—Strong.

*Aspect*.—About 35° to 45° from vertical.

*Texture and luster*.—Smooth, glabrous; glossy.

*Color, when developing and fully developed*.—Close to 187A.

Leaf description:

*Arrangement*.—Opposite or in whorls of four or five leaves; simple.

*Length*.—About 8.6 cm.

*Width*.—About 3.3 cm.

*Shape*.—Elliptical.

*Apex*.—Acuminate.

*Base*.—Attenuate.

*Margin*.—Entire with ciliation.

*Texture and luster, upper surface*.—Smooth, glabrous; slightly glossy to matte.

*Texture and luster, lower surface*.—Smooth, glabrous; somewhat glossy.

*Venation pattern*.—Pinnate; arcuate.

*Color*.—Developing leaves, upper surface: Close to N137A. Developing leaves, lower surface: Close to 148A. Fully expanded leaves, upper surface: Close to N137A; venation, close to 183B. Fully expanded leaves, lower surface: Close to 148A; venation, close to 183A.

*Petioles*.—Length: About 2.7 cm. Diameter: About 3 mm. Strength: Strong. Texture, upper and lower surfaces: Smooth, glabrous; somewhat glossy. Color, upper surface: Close to 183A. Color, lower surface: Close to 185A.

Flower description:

*Flower type and flowering habit*.—Large single rounded and mostly flat axillary flowers; freely flowering habit, typically at least 140 flowers develop per plant; flowers positioned above and beyond the foliar plane; flowers typically face mostly upright to outwardly.

*Flower longevity*.—Flowers typically last about two to three days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about ten weeks after planting.

*Flower buds*.—Length: About 2.2 cm. Diameter: About 1.6 cm. Shape: Ovate. Texture and luster: Smooth, glabrous; somewhat glossy. Color: Close to 53C.

*Flower diameter*.—About 5.6 cm by 5.7 cm.

*Flower depth*.—About 2 cm; with spur, about 4.3 cm.

*Petals*.—Quantity and arrangement: Five per flower in a single whorl. Banner petals, length: About 2.7 cm. Banner petals, width: About 3.7 cm. Lateral petals, length: About 2.8 cm. Lateral petals, width: About 2.6 cm. Lower petals, length: About 3.5 cm. Lower petals, width: About 3.3 cm. Shape: Cordate. Apex: Emarginate. Base: Attenuate. Margin: Entire. Texture and luster, upper and lower surfaces: Smooth, glabrous; velvety; matte. Color: When opening, upper surface: Close to 53B. When opening, lower surface: Close to 53D. Fully opened, upper surface: Close to 53B to 53C; towards the base, close to 185B; venation, close to 53C; color does not change with development. Fully opened, lower surface: Close to 53C; venation, close to 53C; color does not change with development.

*Sepals*.—Quantity and arrangement: Three in a single whorl; two lateral sepals and one center sepal modified into an elongated spur. Lateral sepals, length: About 1 cm. Lateral sepals, width: About 5 mm. Center sepals, length: About 1.8 cm. Center sepals, width: About 1.2 cm. Shape: Elliptical. Apex: Acuminate. Base: Truncate; center sepal modified into a curved spur. Margin: Entire. Texture and luster, upper and lower surfaces: Smooth, glabrous; matte. Color: When opening, upper surface: Close to 54A to 54B. When opening, lower surface: Close to 53C to 53D. Fully opened, upper surface: Close to 63A. Fully opened, lower surface: Close to 63A to 63B. Spur length: About 4.7 cm. Spur diameter: At the flower, about 2 mm. Spur texture and luster: Smooth, glabrous; somewhat glossy. Spur color: Close to 185A.

*Peduncles*.—Length: About 4.8 cm. Diameter: About 2 mm. Angle: About 45° to 55° from branch axis. Strength: Strong. Texture and luster: Smooth, glabrous; somewhat glossy. Color: Close to 185A.

*Reproductive organs*.—Stamens: Quantity: Five fused at anthers; filaments free. Filament length: About 2 mm. Filament color: Close to 60A. Anther size: About 3 mm by 5 mm. Anther shape: Oblong. Anther color: Close to 60A. Pollen amount: Moderate. Pollen color: Close to 158B. Pistils: Quantity per flower: One. Pistil length: About 7 mm. Stigma diameter: About 1.5 mm. Stigma shape: Rounded. Stigma color: Close to 63C. Style length: About 1 mm. Style color: Close to 63C. Ovary color: Close to 187B.

*Seeds and fruits*.—Seed and fruit production has not been observed on plants of the new *Impatiens* to date.

Pathogen & pest resistance: Plants of the new *Impatiens* have not been observed to be resistant to pathogens and pests common to *Impatiens* plants to date.

Garden performance: Plants of the new *Impatiens* have been observed to have good garden performance and tolerate temperatures ranging from about 5° C. to about 40° C.

It is claimed:

1. A new and distinct *Impatiens* plant named 'Duessprspk' as illustrated and described.

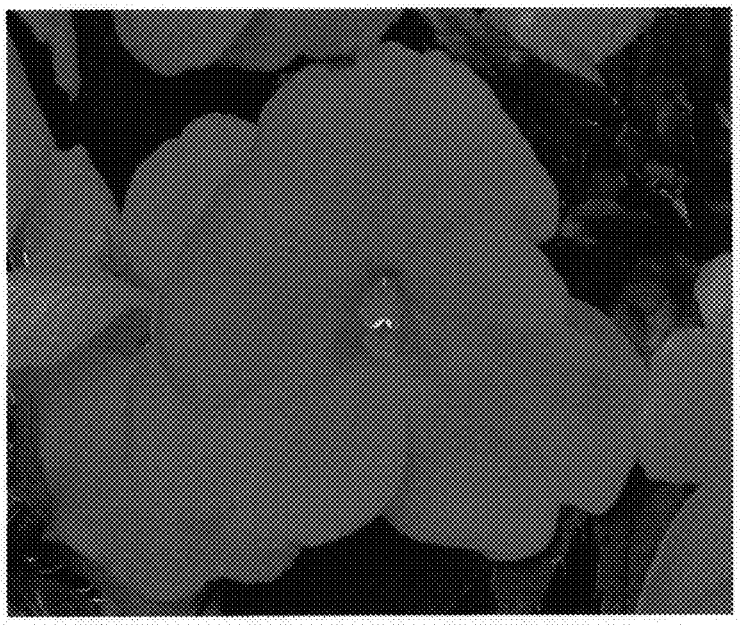
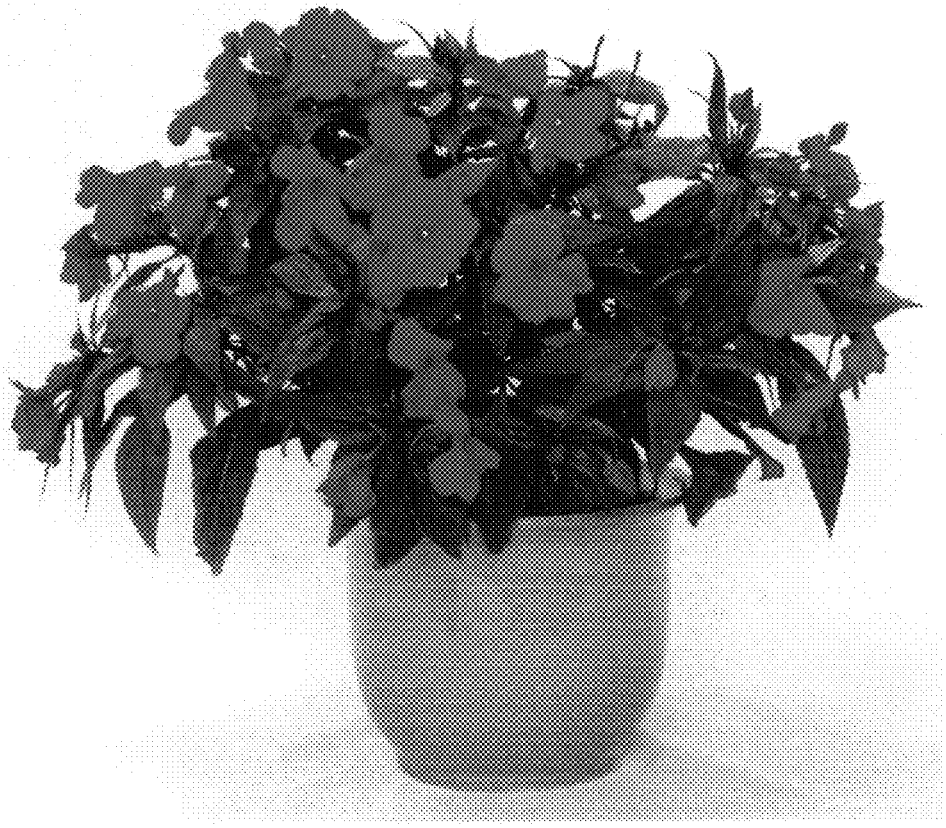

* * * * *